United States Patent

Molinaro et al.

[11] Patent Number: 4,870,194
[45] Date of Patent: Sep. 26, 1989

[54] PROCESS FOR THE PREPARATION AND RECOVERY OF OXDIPHTHALIC ANHYDRIDES

[75] Inventors: John R. Molinaro, Kenmore; Joseph A. Pawlak, Cheektowaga; Willis T. Schwartz, Grand Island, all of N.Y.

[73] Assignee: Occidental Chemical Corporation, Niagara Falls, N.Y.

[21] Appl. No.: 160,036

[22] Filed: Feb. 24, 1988

Related U.S. Application Data

[63] Continuation-in-part of Ser. No. 102,055, Sep. 28, 1987, abandoned.

[51] Int. Cl.⁴ .......................................... C07D 307/89
[52] U.S. Cl. .................................................... 549/241
[58] Field of Search ........................................ 549/241

[56] References Cited

U.S. PATENT DOCUMENTS 4,499,285  2/1985  Evans ............................. 549/241 X
4,625,037  11/1986  Evans ............................. 549/241 X
4,697,023  9/1987  Schwartz et al. .................... 549/241

Primary Examiner—Richard L. Raymond
Attorney, Agent, or Firm—James F. Tao; Arthur S. Cookfair

[57] ABSTRACT

Oxydiphthalic anhydrides of the formula

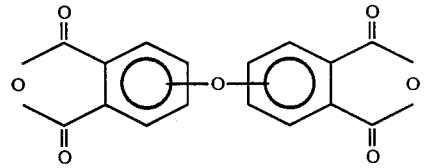

are prepared by reacting a halophthalic anhydride with potassium carbonate in:

(1) a solvent-free reaction medium wherein the molar ratio of halophthalic anhydride:potassium carbonate is greater than 2:1; or (2) a high boiling solvent which improves the mixing of the components, and aids in subsequent purification of the product. The molar ratio of halophthalic anhydride to potassium carbonate is about 1.5:1 or greater.

The oxydiphthalic anhydride can be purified by filtering or centrifuging a hot solution of the oxydiphthalic anhydride in a high boiling solvent to remove impurities, followed by cooling the solution to precipitate the oxydiphthalic anhydride, which can be removed from the solution by filtration or centrifuging.

8 Claims, No Drawings

PROCESS FOR THE PREPARATION AND RECOVERY OF OXDIPHTHALIC ANHYDRIDES

BACKGROUND OF THE INVENTION AND INFORMATION DISCLOSURE STATEMENT

This is a continuation-in-part of application Ser. No. 102,055, filed Sept. 28, 1987, now abandoned.

FIELD OF INVENTION

This invention relates to a method for the preparation of oxydiphthalic anhydrides. The products are useful chemical intermediates for the further preparation of various compounds such as the corresponding dicarboxylic acids and the various derivatives thereof, including for example, the salts, esters, acyl halides, amides, imides and the like. The oxydiphthalic anhydrides are particularly useful as monomers in the preparation of polyimides, for example by polycondensation with a suitable diamine, such as ethylenediamine or phenylenediamine.

PRIOR ART

Various methods for the preparation of oxydiphthalic anhydrides have been described in the chemical literature. In such methods, shown to be useful in the preparation of oxy-diphthalic acids and anhydrides, involves the oxidation of tetramethyl diphenyl ethers. See Kolesnikov et al, *Vysokomol. Soyed*, A9, 612–18 (1967); Marvel et al, *J. Am. Chem. Soc.*, 80, 1197 (1958); and Lavrova et al, *Volokna Sin. Polim.*, 15–24 (1970).

Three Japanese patents to Mitsui describe preparations based on reactions of substituted phthalic anhydrides. Japanese Patent Document 80/136, 246 (Chem. Abst. 95: 42680) teaches the coupling of 4-nitrophthalic anhydride in the presence of sodium nitrite to form 4,4'-oxydiphthalic anhydride. In Japanese Patent Document 80/122, 738 (Chem. Abst. 94: 83799) Mitsui disclose the reaction of 4-halophthalic acid or anhydride with a base to yield 4,4'-oxydiphthalic anhydride. In Japanese Patent Document 80/127, 343 (Chem. Abst. 94: 191942) the reaction of 4-halophthalic anhydride, $Na_2CO_3$ and $NaNO_2$ in dimethyl sulfoxide to form 4,4'-dihydroxydiphthalylic anhydride is described.

German Patent No. 2,416,594 (1975) discloses the coupling of 3-nitrophthalic anhydride in the presence of metal nitrites, such as sodium nitrite to form 3,3'-oxydiphthalic anhydride.

R. L. Markezich and O. S. Zamek, *J. Org. Chem.*, 42, 3431 (1977) describe reaction of 4-nitrophthalimide with potassium fluoride in dimethylsulfoxide to form the corresponding oxydiphthalimide which may be converted by hydrolysis to form the acid and ring closure to form the dianhydride.

U.S. Pat. No. 4,499,285 to T. L. Evans, teaches the solvent-free preparation of thioetherbis(phthalic anhydrides) by reaction of an alkali metal sulfide or alkali metal hydrogen sulfide with a halo- or nitro-substituted phthalic anhydride in the presence of a phase-transfer catalyst such as tetraalkylphosphonium bromide, tetraphenylphosphonium bromide, tetraalkylammonium chloride, 18-crown-6 or others.

U.S. Pat. No. 4,697,023 to Willis T. Schwartz and Joseph A. Pawlak, discloses a process for the preparation of oxydiphthalic anhydrides by reaction of a halophthalic anhydride with water and an alkali metal compound such as potassium fluoride, cesium fluoride or potassium carbonate in the presence of a polar, aprotic solvent. The major disadvantage of this process is the recovery of the product.

Pending patent application Ser. No. 102,055, filed Sept. 28, 1987, now abandoned, discloses the reaction of halophthalic anhydrides with potassium carbonate without a solvent and optionally the addition of potassium fluoride or cerium fluoride as catalysts.

SUMMARY OF THE INVENTION

It has now been found that diphthalic ether dianhydrides of the formula:

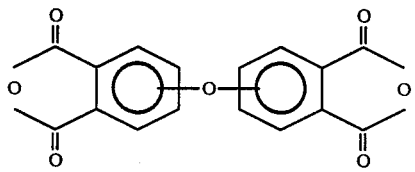

can be prepared by the neat reaction of a halophthalic anhydride of the formula

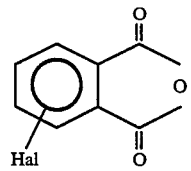

where Hal is F, Cl, Br or I, with potassium carbonate in a reaction medium comprising a molar ratio of halophthalic anhydride to potassium carbonate of greater than 2 to 1.

The process can be carried out in the presence of a catalyst for the reaction. The preferred catalyst is tetraphenylphosphonium bromide.

The process can be carried out in the presence of a solvent that is a liquid at a temperature in the range of about 30° C. to the reaction temperature, that is non-deleterious to the reaction, that is a good solvent for the anhydride product at the reaction temperature, but is a poor solvent for the anhydride product at about 30° C. The preferred solvent is 1,2,4-trichlorobenzene.

The oxydiphthalic anhydrides can be purified by filtering at an elevated temperature a solution of the oxydiphthalic anhydride in a solvent that is a liquid at a temperature in the range of about 30° C. to the reaction temperature, such as up to about 250° C.; and that is a good solvent for the anhydride product at the reaction temperature but a poor solvent for the anhydride product at about 30° C. Then the solution is cooled to a temperature sufficiently low to precipitate the oxydiphthalic anhydride; followed by removing the oxydiphthalic anhydride from the solution by suitable methods such as filtration or centrifuging. Both the oxydiphthalic anhydrides produced by the neat reaction, and also by the solvent reaction may be purified by this process.

DESCRIPTION OF EMBODIMENTS

In the process of the invention, the halogen atom on the halophthalic anhydride reactant functions as a leaving group and becomes the site for the formation of the ether bridge. Thus, when the reactant is a 4-halophthalic anhydride such as

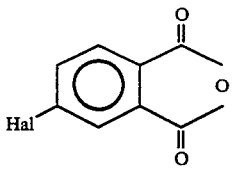

where Hal is F, Cl, Br, or I, the oxydiphthalic product will be 4,4'-oxydiphthalic anhydride characterized by the formula

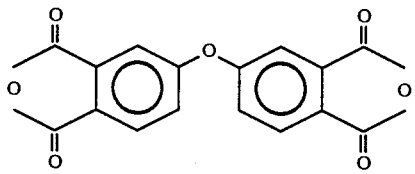

When the reactant is 3-halophthalic anhydride, the oxydiphthalic product will be 3,3'-oxydiphthalic anhydride, characterized by the formula

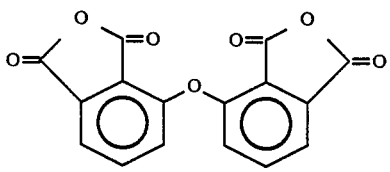

Alternatively, a mixture of the 3-halo- and 4-halophthalic anhydrides may be employed as the starting reactant, to form, in addition to the 4,4'- and 3,3'-oxydiphthalic anhydride isomers, and a 3,4'-oxydiphthalic anhydride of the formula

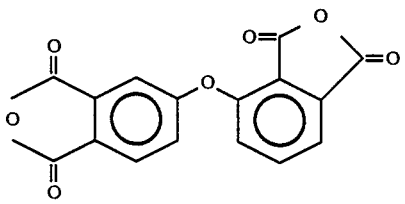

The halogen substituent on the starting halophthalic anhydride reactant may be F, Cl, Br or I. The preferred reactant, based on economic as well as chemical considerations, is 4-fluoro- or 4-chlorophthalic anhydride. In the neat reaction, the halophthalic anhydride reactant is employed in a stoichiometric excess, that is in a molar ratio of halophthalic anhydride:potassium carbonate of greater than 2:1. Typically, a molar ratio of about 2.5:1 to about 5:1 is employed and preferably about 3:1 to about 5:1. In the solvent reaction, the molar ratio of halophthalic anhydride to potassium carbonate is about 1.5:1 or greater, preferably about 2:1 or greater. Typically, a molar ratio of about 2:1 to about 5:1 is employed. It will be appreciated that higher ratios may be employed, with no definite upper limit except that excessively high ratios provide no additional advantage and require the handling of unnecessarily large quantities of the reactant. The excess halophthalic anhydride can be conveniently recycled.

The process of the invention is preferably carried out at atmospheric pressure, but super-atmospheric pressure, for example under autogeneous conditions may be employed, if desired.

The temperature at which the process is carried out may vary considerably, but will generally be within the range of about 170° to about 250° Celsius. When the anhydride reactant is the 4-halophthalic anhydride, the preferred temperature is in the range of about 190° to about 230° C. For the 3-halophthalic anhydride reactant, the preferred temperature is in the range of about 180° to 210° C.

The catalysts useful in the process of the invention include compounds that are generally known as phase transfer agents or catalysts. Suitable phase transfer agents or catalysts include tetraphenylphosphonium bromide, tetraphenylphosphonium chloride, and tetrabutylphosphonium bromide. Other catalysts can be used such as triphenyl phosphine and triphenyl phosphite. In addition, it has been found that, when the halo substituent is chloro-, bromo-, or iodo-, the incorporation of a catalytic amount of potassium fluoride or cesium fluoride will still further improve the efficiency of the neat reaction. These catalysts can also be used with solvents that do not have a deleterious effect on the reaction. We have found that when the halophthalic anhydride reactant is fluorophthalic anhydride, the addition of KF or CsF provides no special advantage.

Typically, the catalysts are employed in amounts of about 0.1 to about 10 percent and preferably about 0.5 to about 5 percent by weight, based on the total weight of reactants.

Among the advantages resulting from the process of this invention when no solvent is employed, are avoidance of potential interaction of solvents with reactants with possible formation of undesired by-products; the simplification of isolation of the oxydiphthalic anhydride product; and the minimization of solvent costs; subsequent disposal and attendant environmental problems.

When a solvent is used for the reaction, the solvent is a liquid and is a poor solvent for the oxydiphthalic anhydride at about 30° C., and is still a liquid, but exhibits good solvent properties at the reaction temperatures of about 170° to 250° C. This solvent should be essentially inert under the conditions of reaction and possess a high boiling point to permit reactions at the preferred temperature at atmospheric pressure. The solvent facilitates the removal of inorganic salts from the dissolved oxydiphthalic anhydride by filtration at elevated temperatures such as about 150° to 250° C., preferably about 150° to 210° C., and the recovery of the product at around room temperature by precipitation. 1,2,4-Trichlorobenzene passes these criteria. 4,4'-Oxydiphthalic anhydride is completely soluble in a 25 percent solution at 170° C., but essentially insoluble at room temperature. Gas chromatographic analysis shows less than 0.5 percent solubility at room temperature.

Other suitable solvents include 1,2- and 1,3-dichlorobenzenes. The solvents are used in a proportion of about 10 to 500 weight percent of the halophthalic anhydride reactant, preferably about 20 to 100 weight percent.

The above-described process for recovery of oxydiphthalic anhydride from high boiling solvents can also be used to purify the product of the neat reaction. Such a reaction product can be dissolved in a solvent that is a liquid at a temperature in the range of about 30° C. to the reaction temperature, such as up to about 250° C.; and that is a good solvent for the anhydride product at the reaction temperature but a poor solvent for the anhydride product at about 30° C. A preferred solvent is 1,2,4-trichlorobenzene. The solution can be filtered to remove solid impurities, and then cooled to precipitate the oxydiphthalic anhydride which can be filtered from the final solutions.

Any of the products of the invention can be further purified by re-dissolving the solid product in the above-described solvents, for example, 1,2,4-trichlorobenzene, followed by precipitation. Other high boiling solvents such as cyclohexanone can be employed in this re-precipitation or recrystallization process.

The following examples are provided to further illustrate this invention and the manner in which it may be carried out. It will be understood, however, that the specific details given in the examples have been chosen for the purposes of illustration only and are not to be construed as limiting the invention. In the examples, unless otherwise indicated, all parts and percentages are by weight and all temperatures are in degrees Celsius.

EXAMPLE 1

A mixture of a 99.2 percent pure 4-chlorophthalic anhydride* (100.0 grams, 0.543 mole), and potassium carbonate (18.9 grams, 0.137 mole) was heated in a nitrogen atmosphere to about 229° C., with stirring. Samples were withdrawn periodically and analyzed by gas chromatographic techniques, with the following results:
*Prepared by decarbonylation of trimellitic anhydride with Pd/C following the procedure of Verbicky, Dellacoletta and Williams, *Tetrahedron Letters*, Vol. 23, No. 4, pp. 371–372, (1982). The decarbonylated product was purified by distillation and recrystallization. This procedure was used in all other examples except as noted.

| Reaction Time (Hours) | Reaction Temperature (°C.) | 4-Chlorophthalic Anhydride (Area %) | 4,4'-Oxydiphthalic Anhydride (Area %) |
|---|---|---|---|
| 5.0 | 228 | 97.3 | 2.7 |
| 6.0 | 230 | 94.8 | 5.2 |
| 7.0 | 228 | 89.3 | 9.0 |
| 10.0 | 229 | 77.6 | 22.3 |
| 13.0 | 227 | 61.8 | 38.1 |
| 15.2 | 227 | 53.5 | 46.5 |
| 17.2 | 229 | 52.5 | 46.5 |

EXAMPLE 2

A mixture of 98.3 percent pure 4-chlorophthalic anhydride (105 grams, 0.570 mole) and potassium fluoride (2.5 grams, 0.043 mole) was heated to about 229° C. and potassium carbonate (19.8 grams, 0.143 mole) was added over a 65-minute period. Following the addition of potassium carbonate, the mixture was held at about 230° C. with periodic sampling and analyses by gas chromatographic methods with the following results:

| Reaction Time (Hours) | Reaction Temperature (°C.) | 4-Chlorophthalic Anhydride (Area %) | 4,4'-Oxydiphthalic Anhydride (Area %) |
|---|---|---|---|
| 0.0 | 231 | 93.9 | 1.8 |
| 1.0 | 228 | 92.6 | 2.6 |
| 2.3 | 230 | 89.8 | 5.5 |
| 5.0 | 230 | 78.7 | 17.9 |
| 6.0 | 231 | 74.6 | 22.7 |
| 7.0 | 228 | 68.1 | 29.4 |
| 8.8 | 229 | 56.5 | 41.4 |
| 9.8 | 229 | 50.8 | 47.4 |

EXAMPLE 3

A mixture of 99.2 percent pure 4-chlorophthalic anhydride (105.4 grams, 0.573 mole), cesium fluoride (1.0385 grams, 6.836×10$^{-3}$ mole) and potassium carbonate (19.8 grams, 0.143 mole) was heated to about 220° C. When the temperature reached 220° C., the reaction exothermed to 235° C. The mixture appeared to have gelled, however, on further reaction, the mixture began to slowly decrease in viscosity. After 4.1 hours at 218°–235° C., GC area percent analyses showed that the mixture contained 47.4 percent of the 4-chlorophthalic anhydride and 51.8 percent of the 4,4'-oxydiphthalic anhydride.

EXAMPLE 4

A 93.2 percent pure 4-bromophthalic anhydride+ (100.0 grams, 0.411 mole) was heated with stirring to 212° C. and purged with nitrogen for 25 minutes at 212° to 231° C. to expel any water vapor. Tetraphenylphosphonium bromide (0.60 grams, 1.43×10$^{-3}$ mole) was added to the hot 4-bromophthalic anhydride. Potassium carbonate (14.2 grams, 0.103 mole) was added to the hot mixture over a 65-minute period at 230° to 233° C. A sample withdrawn immediately after the potassium carbonate addition analyzed by GC as having 76 percent 4-bromophthalic and 19.9 percent 4,4'-oxydiphthalic anhydride. After an additional one-hour at 230° C., the 4-bromophthalic anhydride content decreased to 49.5 percent while the 4,4'-oxydiphthalic anhydride content increased to 46.7 percent.
+Made by bromination of phthalic acid in the presence of sodium hydroxide.

EXAMPLE 5

A 97.8 percent pure 4-fluorophthalic anhydride++ (100.0 grams, 0.589 mole) was heated with stirring under a nitrogen pad to 227° C. and 0.6 grams (1.43×10$^{-3}$ mole) of the tetraphenylphosphonium bromide catalyst added. Potassium carbonate (20.3 grams, 0.147 mole) was added over a 59-minute period at 227° to 230° C. Some foaming occurred during the potassium carbonate addition and the mixture became very viscous. After heating for one hour at 229° C., the viscosity of the mixture decreased significantly and GC analysis showed the mixture to contain 44.0 percent of the 4-fluorophthalic anhydride and 53.5 percent of 4,4'-oxydiphthalic anhydride.
++Made by reaction of 4-chlorophthalic anhydride with potassium fluoride.

EXAMPLE 6

The reaction of Example 1 was repeated using 0.41 percent of tetraphenylphosphonium bromide by weight of the 4-chlorophthalic anhydride charged. The potassium carbonate, however, was added over a one-hour period and the temperature was lowered to 220° C. The results shown below were quite dramatic in that the reaction was accomplished in a short time of only about 3 hours.

| Reaction Time (Hours) | 4-Chlorophthalic Anhydride (Area %) | 4,4'-Oxydiphthalic Anhydride (Area %) |
|---|---|---|
| 0.0 | 93.8 | 5.3 |
| 0.5 | 89.7 | 9.4 |
| 1.0 | 85.5 | 16.6 |
| 1.5 | 78.3 | 20.8 |
| 2.0 | 69.0 | 29.7 |

| Reaction Time (Hours) | 4-Chlorophthalic Anhydride (Area %) | 4,4'-Oxydiphthalic Anhydride (Area %) |
| --- | --- | --- |
| 3.0 | 52.3 | 46.9 |
| 3.5 | 51.9 | 48.0 |

The final product was a light rose-beige material melting at 225.5° to 226.5° C. The yield was 72.8 percent.

EXAMPLE 7

4-Chlorophthalic anhydride and potassium carbonate were reacted in a mole ratio of anhydride to carbonate of 2 to 1 in 1,2,4-trichlorobenzene. 60.0 Grams of 99 percent pure 4-chlorophthalic anhydride, 22.8 grams of potassium carbonate, 1.2 parts MPEG 2000 (methyl terminated polyethylene glycol with a molecular weight of 2000), were heated in 180.0 grams of 1,2,4-trichlorobenzene to 198° to 200° C. and held 5.4 hours. No product formed. Tetraphenylphosphonium bromide (0.6 grams) was added at room temperature and the batch was reheated to 200° C. The following results were obtained after the catalyst was added.

| Reaction Time (Hours) | 4-Chlorophthalic Anhydride (Area %) | 4,4'-Oxydiphthalic Anhydride (Area %) |
| --- | --- | --- |
| 3.6 | 96.2 | 2.0 |
| 5.0 | 88.5 | 9.6 |
| 11.2 | 57.4 | 40.7 |
| 12.5 | 52.3 | 45.9 |
| 15.4 | 43.7 | 53.9 |
| 17.3 | 36.0 | 61.9 |
| 24.3 | 16.3 | 81.1 |

EXAMPLE 8

The reaction of 4-chlorophthalic anhydride with potassium carbonate in 1,2,4-trichlorobenzene with no catalyst at 210°–215° C. gave no product after 24.5 hours.

EXAMPLE 9

105.0 Grams of 4-chlorophthalic anhydride were charged to a reactor equipped with a stirrer and thermometer. The reactor was heated to 230° C. and then 0.35 gram of tetraphenylphosphonium chloride was added to the reactor and mixed for one minute. 19.8 grams of potassium carbonate were added and the reaction mixture was heated with stirring at 225°–230° C. for 5 hours. A GC analysis of the contents showed it to contain 50.6 percent 4-chlorophthalic anhydride and 48.3 percent 4,4'-oxydiphthalic anhydride.

EXAMPLE 10

25.0 Grams of 4-chlorophthalic anhydride, 10.4 grams of potassium carbonate, 0.5 gram of tetraphenylphosphonium chloride, 0.5 gram of MPEG-2000 (methyl terminated polyethylene glycol with a molecular weight of 2000), and 146.5 grams of 1,2,4-trichlorobenzene were charged to a 500 ml flask equipped with a stirrer and thermometer. The mixture was heated with an oil bath to a temperature in the range of 204° to 205° C. The final reaction mixture after 5 hours consisted of 57.3 percent 4,4'-oxydiphthalic anhydride and 39.4 percent 4-chlorophthalic anhydride by GC area percent.

EXAMPLE 11

105.0 Grams of 4-chlorophthalic anhydride were added to a reactor equipped with a stirrer and thermometer. The contents were heated to 220° C. and 0.63 gram of tetrabutylphosphonium bromide was added. Then 19.8 grams of potassium carbonate were added over a period of 65 minutes. The reaction was continued at about 220° C. for 11 hours at which time GC analysis showed 49.6 percent (by area) 4-chlorophthalic anhydride and 49.6 percent (by area) of 4,4'-oxydiphthalic anhydride in the mixture.

EXAMPLE 12

105.0 Grams of 4-chlorophthalic anhydride were added to a reaction flask equipped with a stirrer and thermometer. The anhydride was heated to 230° C. and 0.31 gram of triphenylphosphine was added. Then 19.8 grams of potassium carbonate were added from a powder funnel over a period of one hour. After 3.5 hours at 230° C., 45.5 percent of 4,4'-oxydiphthalic anhydride was present in the reaction mixture as determined by GC internal standard method. Purification in accord with Example 16, yielded 33.4 grams (83.6 percent yield) of 4,4'-oxydiphthalic anhydride.

EXAMPLE 13

105.0 Grams of 4-chlorophthalic anhydride were charged to a 250 ml reaction flask equipped with a stirrer and thermometer and heated to about 230° C. Then 0.28 grams of triphenylphosphite were added and allowed to mix for one minute. Then 19.8 grams of potassium carbonate were added with a powder funnel. The following results were obtained. 4,4'-Oxydiphthalic anhydride was present at 44.2 area percent after 6 hours at about 230° C. Purification in accord with Example 16, resulted in 71.5 percent yield of 4,4'-oxydiphthalic anhydride.

EXAMPLE 14

18.25 Grams (0.1 mole) of 4-chlorophthalic anhydride** and 0.03 gram of tetraphenylphosphonium bromide (0.165 percent on the 4-chlorophthalic anhydride) were mixed with 6.0 grams of 1,2,4-trichlorobenzene and the mixture heated to 225° C. Potassium carbonate (2.76 grams, 0.02 mole) was added over a period of 10 minutes and the reaction mixture heated at 225° C. for 6 hours. The reaction mixture consisted of 34.1 percent 4,4'-oxydiphthalic anhydride and 63.3 percent 4-chlorophthalic anhydride.

**Made by aromatization of 4-chlorotetrahydrophthalic anhydride, disclosed in SN 160,033 filed on even date herewith.

EXAMPLE 15 A

High purity 3-chlorophthalic anhydride*** (105.3 grams, 0.5767 mole) was charged into a 3-neck, 250 ml Morton flask equipped with a N$_2$ inlet, mechanical stirrer, a Claisen-type adapter, thermometer, gas pressure equalizing tube and a ground glass stopper. The 3-chlorophthalic anhydride was heated to 180° C. and 0.327 gram of tetraphenylphosphonium bromide was added. The 3-chlorophthalic anhydride yellowed slightly upon heating to 180° C., and turned to a deeper yellow color upon the catalyst addition. Potassium carbonate (17.8 grams, 0.1288 mole) was added over a 53-minute period at 180° to 180.5° C. The reaction mixture was kept at 180° C. and samples were withdrawn immediately after the potassium carbonate addition and periodically afterwards for GC area percent analyses. The results of these analyses are given below.

***The 3-chlorophthalic anhydride was prepared by the chlorodenitration of 3-nitrophthalic anhydride.

| Time (Hours) | 3-Chlorophthalic Anhydride | 3,3'-Oxydiphthalic Anhydride |
|---|---|---|
| 0 | 99.8 | 0.0 |
| 1.0 | 97.8 | 1.6 |
| 2.0 | 92.3 | 6.9 |
| 3.0 | 86.8 | 12.7 |
| 4.0 | 81.7 | 17.6 |
| 5.5 | 72.4 | 26.4 |
| 6.5 | 67.9 | 30.9 |
| 7.5 | 62.6 | 35.5 |
| 8.25 | 59.5 | 39.5 |

EXAMPLE 15B

50 Grams of 3-chlorophthalic anhydride* and 50 grams of 4-chlorophthalic anhydride were added to the reactor of Example 15A together with 0.33 grams tetraphenylphosphonium bromide. 9.3 Grams of potassium carbonate were added to the reactor over a period of one hour at about 230° C. Another 9.3 grams of potassium carbonate were added after 3 hours. The reaction mixture was kept at about 230° C. After 4 hours, a GC (gas chromotography) analysis of the reaction mixture showed it contained about 12.6 percent of 3,3'-oxydiphthalic anhydride, about 21.1 percent of 3,4'-oxydiphthalic anhydride and 7.8 percent of 4,4'-oxydiphthalic anhydride. The product was purified by adding 70 grams hot 1,2,4-trichlorobenzene, and filtering the resulting solution. The filter cake was rinsed with 130 grams of 1,2,4-trichlorobenzene. The temperature of the solution was cooled to precipitate the product, which was analyzed by GC and found to contain 43.2 percent of 3,3'-oxydiphthalic anhydride, 47.8 percent of 3,4'-oxydiphthalic anhydride and 2.7 percent of 4,4'-oxydiphthalic anhydride. After drying in the oven, the yield was 16.8 grams or 40.2 percent of theory.

***The 3-chlorophthalic anhydride was prepared by the chlorodenitration of 3-nitrophthalic anhydride.
**Made by aromatization of 4-chlorotetrahydrophthalic anhydride, disclosed in SN 160,033.

EXAMPLE 16

A mixture of 18.2 grams (0.1 mole) of 4-chlorophthalic anhydride** and 4.2 grams of 1,2,4-trichlorobenzene were heated to 222° C. Granular potassium carbonate 3.45 grams (0.025 mole) was added and the mixture heated with stirring at 222° to 224° C. for eight hours. A GC analysis of the reaction mixture showed it to contain 52.2 percent (area) of 4,4'-oxydiphthalic anhydride. The theoretical content should be 50 percent.

**Made by aromatization of 4-chlorotetrahydrophthalic anhydride, disclosed in SN 160,033.

EXAMPLE 17

The product of Example 1 was purified by the following method. To remove the insoluble materials in the reaction mixture, 200.7 grams of 1,2,4-trichlorobenzene (TCB) was added to the solid product and heated to about 200° C., and mixed well. The resulting hot mixture was then filtered through a glass Buchner funnel. The resulting filter cake then rinsed with about 144 grams of hot TCB (200° C.) and both filtrates combined. This hot solution was then allowed to cool with agitation. After cooling the filtrate to room temperature, the product had precipitated and was collected by filtration. The solids were then washed with about 107 grams of cold TCB and dried in an air circulating oven at about 145° C. overnight. 32.9 Grams of 4,4'-oxydiphthalic anhydride were recovered, reflecting a yield of 77.6 percent based on the $K_2CO_3$.

EXAMPLE 18

75 Grams of 1,2,4-trichlorobenzene (TCB) was added to the reaction mixture of Example 9. After heating to 200° C., the contents were filtered and the filtrate allowed to cool. The solids which crystallized were removed by filtration, washed with cold TCB and n-hexane and dried giving 36.2 grams of product (81.3 percent yield based on $K_2CO_3$).

EXAMPLE 19

The product of Example 11 was treated with 104.0 grams of hot 1,2,4-trichlorobenzene and the mixture reheated to 210° C. After filtration hot, the filter cake was washed with an additional 100 grams of hot 1,2,4-trichlorobenzene, filtered and the filtrates combined. After cooling to room temperature, the product which crystallized was recovered by filtration and dried. The yield was 36.6 grams or 82.2 percent of theory.

EXAMPLE 20

To the reaction product of Example 14 was added 12 grams of hot 1,2,4-trichlorobenzene. The solution at 200° C. was filtered to remove inorganic salts. The filter cake was washed with another 6 grams of hot 1,2,4-trichlorobenzene. The combined filtrates were allowed to cool to precipitate the 4,4'-oxydiphthalic anhydride product. Filtration of the product followed by drying yielded 5.5 grams (88.7 percent yield) of 4,4'-oxydiphthalic anhydride.

EXAMPLE 21

The flask contents in Example 16 was treated with 18.0 grams of refluxing cyclohexanone (157° C.) The solids were filtered off, and washed with another 18.0 grams of hot cyclohexanone and again filtered. The filtrates were combined and allowed to cool to permit crystallization of the product, which was removed by filtration. After washing with 15 ml of 1,2,4-trichlorobenzene and 25 ml of hexane followed by drying, 7.25 grams (93.5 percent yield) of 4,4'-oxydiphthalic anhydride were obtained.

What is claimed is:

1. A process for the purification of oxydiphthalic anhydride prepared by reacting halophthalic anhydride and potassium carbonate in a neat reaction wherein the molar ratio of halophthalic anhydride:potassium carbonate is greater than 2:1; which comprises:
   (1) filtering at a temperature of about 150° to 250° Celsius a solution of the oxydiphthalic anhydride in 1,2,4-trichlorobenzene to remove the solid impurities from the solution,
   (2) cooling the resulting solution to a temperature of below about 30° Celsius to precipitate the oxydiphthalic anhydride, and
   (3) removing the oxydiphthalic anhydride from the solution.

2. The process of claim 1 wherein the oxydiphthalic anhydride is removed from the solution in step (3) by filtration.

3. The process for the preparation and purification of oxydiphthalic anhydride which comprises:
   (1) reacting a 4-halophthalic anhydride with potassium carbonate, in a neat reaction wherein the molar ratio of 4-halophthalic anhydride:potassium carbonate is greater than 2:1, dissolving the resultant oxydiphthalic anhydride product in 1,2,4-trichlorobenzene, at a temperature of about 150° to 250° Celsius, (2) removing solid impurities from the hot solution, (3) cooling the resulting solution to precipitate the oxydiphthalic anhydride, and (4) removing the precipitated oxydiphthalic anhydride from the solution.

4. The process of claim 3 wherein the oxydiphthalic anhydride is removed in step (4) by filtration.

5. The process for the purification of the oxydiphthalic anhydride produced by the reaction of a halophthalic anhydride of the formula

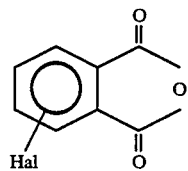

where Hal is F, Cl, Br or I with potassium carbonate in the presence of a catalytic amount of a catalyst for the reaction in a reaction medium comprising a solvent selected from the group consisting of 1,2,4-trichlorobenzene, 1,2-dichlorobenzene, and 1,3-dichlorobenzene which comprises (1) filtering the hot solution of oxydiphthalic anhydride to remove solid impurities, (2) cooling the solution of oxydiphthalic anhydride to precipitate the oxydiphthalic anhydride, and (3) removing the oxydiphthalic anhydride from the solution.

6. The process for the preparation and purification of 4,4'-oxydiphthalic anhydride which comprises:

(1) reacting a 4-halophthalic anhydride with potassium carbonate, in a liquid reaction medium comprising 1,2,4-trichlorobenzene and wherein the molar ratio of 4-halophthalic anhydride to potassium carbonate is about 2:1 or greater; adding an additional amount of 1,2,4-trichlorobenzene at a temperature of about 150° to 250° Celsius, (2) filtering the resulting hot solution of 4,4-oxydiphthalic anhydride in 1,2,4-trichlorobenzene to remove solid impurities therefrom, (3) cooling the resulting solution to precipitate the oxydiphthalic anhydride, and (4) removing the precipitated oxydiphthalic anhydride from the solution.

7. The process of claim 6 wherein the oxydiphthalic anhydride is removed in step (4) by filtration.

8. A process for the purification of 4,4'-oxydiphthalic anhydride prepared by the reaction of 4-chlorophthalic anhydride and potassium carbonate in a solvent from the group consisting of 1,2,4-trichlorobenzene, 1,2-dichlorobenzene, 1,3-dichlorobenzene, and mixtures thereof in a molar ratio of 4-chlorophthalic anhydride:potassium carbonate of greater than 2:1 to form a solution of crude reaction product said purification process consisting essentially of (1) removing solid impurities by filtering the solution at a temperature of about 150° C. to 250° C., (2) cooling the solution to below about 30° C. to precipitate oxydiphthalic anhydride, (3) removing the precipitated oxydiphthalic anhydride by filtration.

* * * * *